United States Patent
Dai et al.

(10) Patent No.: US 8,521,287 B2
(45) Date of Patent: Aug. 27, 2013

(54) POWER SCHEME FOR IMPLANT STIMULATORS ON THE HUMAN OR ANIMAL BODY

(75) Inventors: Rongqing Dai, Valencia, CA (US); Robert J. Greenberg, Los Angeles, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 273 days.

(21) Appl. No.: 11/924,504

(22) Filed: Oct. 25, 2007

(65) Prior Publication Data
US 2008/0114231 A1    May 15, 2008

Related U.S. Application Data

(62) Division of application No. 11/598,965, filed on Nov. 14, 2006.

(51) Int. Cl.
*A61N 1/18* (2006.01)

(52) U.S. Cl.
USPC .............................. 607/29; 607/2

(58) Field of Classification Search
USPC .......................... 607/2, 53, 54, 29
See application file for complete search history.

(56) References Cited

U.S. PATENT DOCUMENTS

| | | | |
|---|---|---|---|
| 4,408,608 A * | 10/1983 | Daly et al. ...................... | 607/57 |
| 4,573,481 A | 3/1986 | Bullara | |
| 4,628,933 A | 12/1986 | Michelson | |
| 4,837,049 A | 6/1989 | Byers et al. | |
| 5,109,844 A | 5/1992 | de Juan, Jr. et al. | |
| 5,215,088 A | 6/1993 | Normann et al. | |
| 5,876,425 A * | 3/1999 | Gord et al. ...................... | 607/56 |
| 5,935,155 A | 8/1999 | Humayun et al. | |
| 6,393,327 B1 | 5/2002 | Scribner | |
| 6,400,989 B1 | 6/2002 | Eckmiller | |
| 6,458,157 B1 | 10/2002 | Suaning | |
| 2002/0091421 A1* | 7/2002 | Greenberg et al. ............. | 607/54 |
| 2003/0130699 A1* | 7/2003 | Kelly et al. ....................... | 607/5 |
| 2007/0255319 A1 | 11/2007 | Greenberg et al. | |

FOREIGN PATENT DOCUMENTS

WO    WO 2005/118064 A2    12/2005

OTHER PUBLICATIONS

Jung, Walter G. "Don't Shun the Shunt Regulator." Electronic Design 14. Jul. 5, 1969. pp. 70-72.*
De Juan, Retinal Tacks, American Journal of Ophthalmology 99, pp. 272-274, Mar. 1985.
Liu, et al., A Neuro-Stimulus Chip with Telemetry Unit for Retinal Prosthetic Device, IEEE Journal of Solid-State Circuits, vol. 35 No. 10, pp. 1487-1497, Oct. 2000.
Final Office Action dated Oct. 19, 2011 for U.S. Appl. No. 11/598,965, filed Nov. 14, 2006.
Advisory Action dated Feb. 7, 2012 for U.S. Appl. No. 11/598,965, filed Nov. 14, 2006.

* cited by examiner

*Primary Examiner* — Allen Porter, Jr.
(74) *Attorney, Agent, or Firm* — Scott B. Dunbar; Alessandro Steinfl (57) ABSTRACT

A power scheme for an implant on a human or animal body comprises: a charging circuit to provide power to deliver controlled stimulation currents to a body tissue; a capacitive storage arrangement connected with the charging circuit and charged by the charging circuit; a shunting arrangement to limit voltage on the capacitive storage arrangement; a driver array configured to transfer charges from the capacitive storage arrangement to the tissue; and an electrode array connected with the driver array and the tissue.

5 Claims, 11 Drawing Sheets

POWER SCHEME FOR IMPLANT STIMULATORS ON THE HUMAN OR ANIMAL BODY

CROSS REFERENCE TO RELATED APPLICATIONS

This application is a divisional application of, and claims priority to, U.S. application Ser. No. 11/598,965, filed Nov. 14, 2006, for Power Scheme for Implant Stimulators on the Human or Animal Body.

FEDERALLY SPONSORED RESEARCH

This invention was made with government support under grant No. R24EY12893-01, awarded by the National Institutes of Health. The U.S. Government may have certain rights in the invention.

BACKGROUND

1. Field

The present disclosure relates to implants for humans or animals. In particular, it relates to a power scheme for implant stimulators (also referred to as implants in the present application) on the human or animal body.

2. Related Art

The following paragraphs will introduce some art possibly related to the present application.

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across retinal neuronal cell membranes, which can initiate retinal neuronal action potentials, which are the means of information transfer in the nervous system.

Based on this mechanism, it is possible to input information into the nervous system by coding the sensory information as a sequence of electrical pulses which are relayed to the nervous system via the prosthetic device. In this way, it is possible to provide artificial sensations including vision.

Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the retinal neurons, and avoid undue compression of the retinal neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated a cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Opthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal electrode array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

Retinal implants receiving power from an external unit through an inductive power link coupled through coils are known. When the coil sizes and positioning are limited by the physical conditions, the power delivering efficiency can be reduced dramatically, in which case the maximum power to the implant may be limited. On the other hand, a higher amount of power used by the implant also means a worse condition in terms of thermal dissipation.

Both of the situations above require a reduced power demand by the implant stimulator. For applications that need a large number of stimulation channels, such as in the case retinal prosthesis, the efficiency between the output current and the input power becomes critical.

SUMMARY

According to a first aspect of the present disclosure, a power control system for an implant on a human or animal body is shown, comprising: a charging circuit to provide power to deliver controlled stimulation currents to a tissue of the human or animal body; a capacitive storage arrangement connected with the charging circuit and charged by the charging circuit; a shunting arrangement to limit voltage on the capacitive storage arrangement; a driver array configured to transfer charges from the capacitive storage arrangement to the tissue; and an electrode array connected with the driver array and the tissue.

According to a second aspect of the present disclosure, a shunting circuit to regulate capacitor voltage in an implant for a human or animal body is shown, the implant comprising a capacitive storage arrangement, the shunting circuit comprising: a current sensor comprising terminals connected in parallel with the capacitive storage arrangement, the current sensor sinking current from the capacitive storage arrangement when the voltage of the capacitive storage arrangement reaches a voltage value.

According to a third aspect of the present disclosure, a constant current type electrode driver for an implant for a human or animal body is shown, the electrode driver comprising: a driver controller to generate anodic and cathodic stimulation switching signals and generate an output current defining a current amplitude for stimulation; a conversion circuit to convert the output current into an anodic current or a cathodic current; and a switching arrangement to allow selection between the anodic current or the cathodic current.

According to a fourth aspect of the present disclosure, a compliance monitoring circuit to monitor and control compliance voltage of an electrode contacting a tissue of a human or animal body is shown, the electrode being connected with an electrode driver comprising an output MOSFET transistor having a drain-source voltage Vds, a gate-source voltage Vgs and a threshold voltage Vt, the compliance monitoring circuit monitoring a condition Vgs−Vds>Vt and generates an alert signal when such condition is met.

According to a fifth aspect of the present disclosure, a power monitor to monitor charging and draining conditions of i) a capacitive storage arrangement and ii) shunting circuits comprised in an implant for a human or animal body is shown, the power monitor comprising: a current monitor, the current monitor comprising an analog to digital converter digitizing analog inputs from the shunting circuits and outputting an output current level; and a capacitor monitoring circuit, to monitor whether implant power falls below a power value.

According to a sixth aspect of the present disclosure, a method to control power in an implant for a human or animal body is shown, the implant comprising electrodes contacting a tissue of the body, the method comprising: capacitively storing electric charges; providing the electric charges to the electrodes; monitoring when the electric charges are above a high value or below a low value; and controlling the electric charges when above the high value or below the low value.

According to a seventh aspect of the present disclosure, a circuit is shown, comprising: an electrode driver array; storage capacitors connected with the electrode driver array, wherein charge stored on the storage capacitors is adapted to be transferred to an array of electrodes connected with the electrode driver array; a charging circuit charging the storage capacitors; and a monitoring circuit to continuously monitor voltage on the storage capacitors and to control at least one between the electrode driver array and the charging circuit based on the voltage.

BRIEF DESCRIPTION OF THE DRAWINGS

FIGS. 1-1, 1-2 and 1-3, to be seen as connected side by side, show a general diagram of the implant power control scheme in accordance with the present disclosure.

FIGS. 8-1 and 8-2, to be seen as connected side by side, are a flow chart showing the power control flow of the scheme shown in FIG. 1.

DETAILED DESCRIPTION

Figure 11:
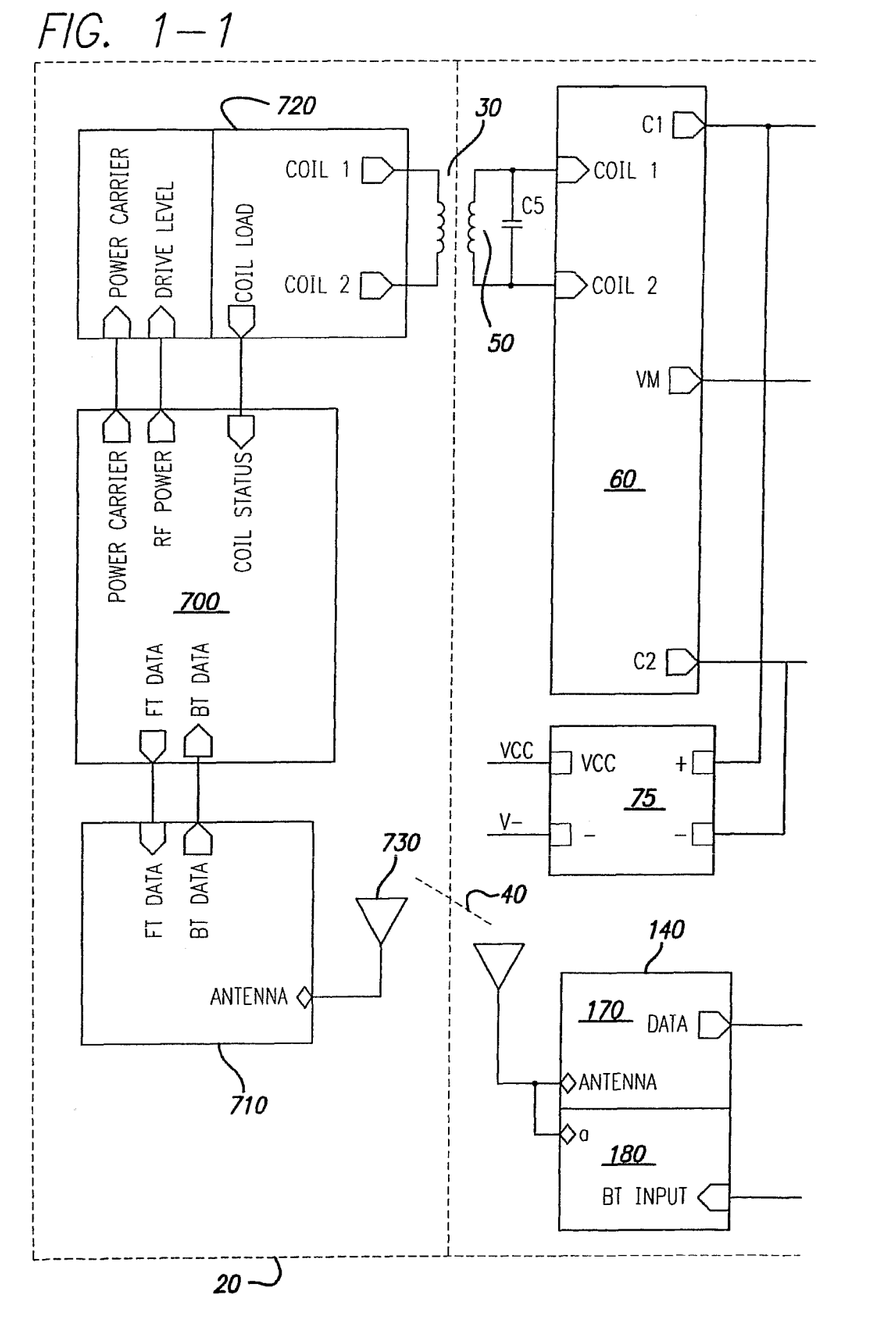
Figure 12:
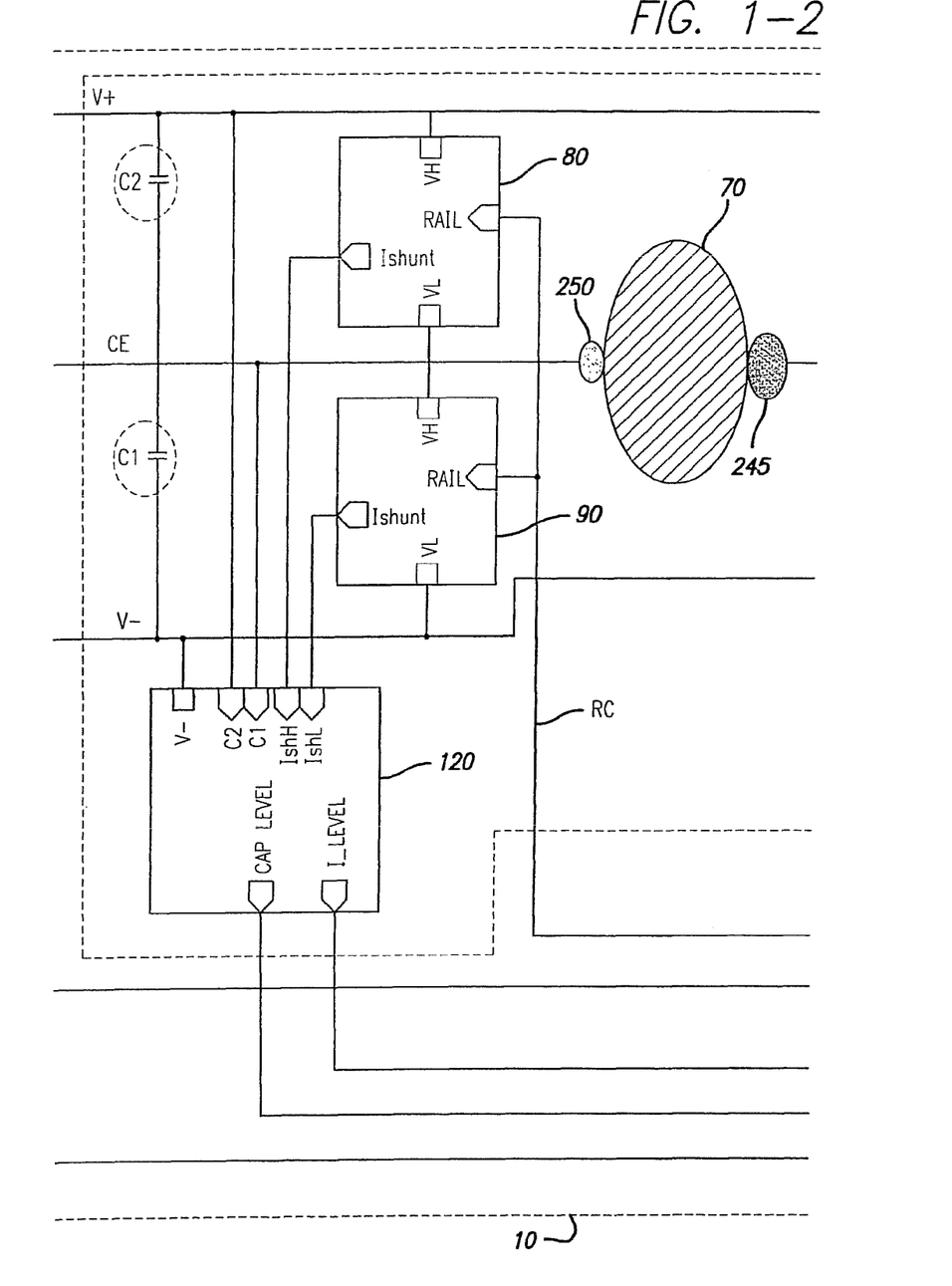
Figure 13:
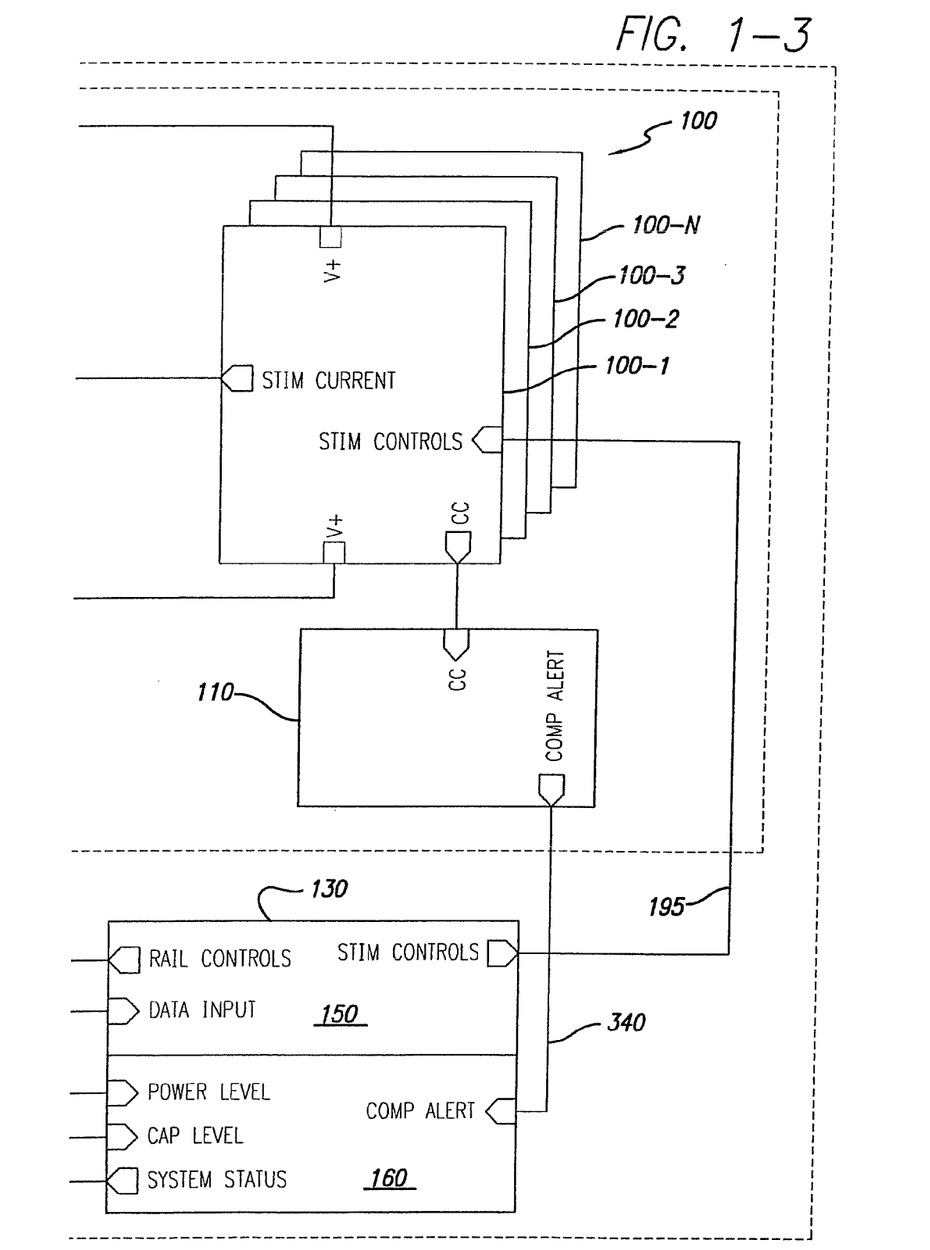

FIGS. 1-1, 1-2 and 1-3 are a diagram of an implant power control scheme in accordance with an embodiment of the present disclosure.

A retinal implant 10 receives power from an external unit 20 through an inductive power link 30 coupled through coils. Control and status information are exchanged between retinal implant 10 and external unit 20 through data link 40. While the embodiment of FIGS. 1-1, 1-2, 1-3 and the following figures is concerned with a retinal implant, the person skilled in the art will appreciate that the same scheme can be used also for other types of implants on the human or animal body, such as cochlear implants or implants to restore neuronal functions impaired due to injuries or diseases.

Power at the implant side is received by implant coil 50. Implant coil 50 is tunable with capacitor C3 to the power carrier frequency. The received AC power is converted into DC power by a rectifier circuit 60. Rectifier circuits are known per se to the person skilled in the art. In the case at issue, the rectifier circuit 60 can comprise, by way of example, diode bridges or MOSFET circuits.

The output V+, VM, V− of rectifier circuit 60 provides the power to deliver controlled stimulation currents to the tissue 70. A small portion of the output of rectifier 60 can be tapped out or diverted to supply circuits for other operations through a regulator circuit 75. Such operations can include RF data receiving and transmitting, logic control, signal measurements and so on.

The output of rectifier circuit 60 continuously charges two capacitive storage arrangements which are shown as C1 and C2 in FIG. 1-2 provided to supply all electrode drivers for bi-phase or multi-phase stimulation. Those capacitive arrangements could also be represented as arrays of capacitors or storage devices based on a capacitive behavior to boost output power.

Figure 2:
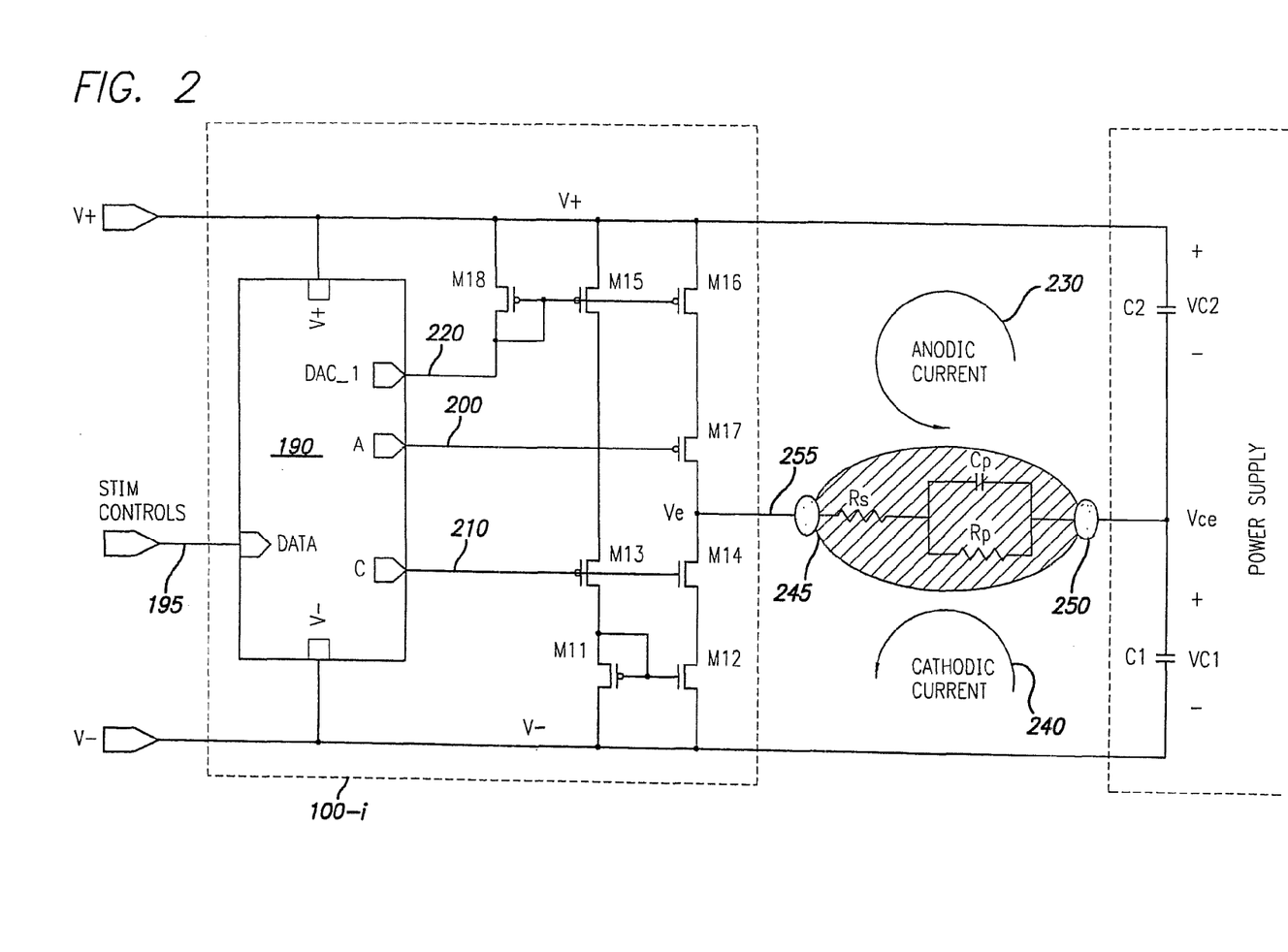
FIG. 2 shows a circuital scheme of an electrode driver.

The voltages of C1 and C2 are limited by shunt regulator circuits 80 and 90, respectively. The charge stored on C1 and C2 is transferred to the tissue 70 through a plurality of electrode drivers 100-i forming a driver array 100 comprised of electrode drivers 100-1, 100-2, . . . , 100-i, . . . 100-n. The drivers act as a controlled energy transporter to allow stimulation of the tissue 70 in form of bursts of biphasic (anodic and cathodic) current pulses. Each driver can comprise, for example, a constant current source or sink circuit, as later shown in FIG. 2. Each driver is connected to a respective stimulation electrode 245-i (see also FIG. 2). The plurality of stimulation electrodes 245-i forms a stimulating electrode array 245 in direct contact with the tissue 70, as shown in FIG. 1-2. As also explained above, while the present embodiment makes reference to a retinal tissue, other types of human or animal tissue can be envisaged by the person skilled in the art.

The present disclosure provides for monitoring and control of excessively low capacitor voltage. In particular, when charges are transferred from capacitors C1, C2 to the tissue 70, the voltage on the capacitors drops. A minimum value for this voltage is defined by a so-called compliance voltage. The compliance voltage is defined by the electrode-tissue impedance at the interface 245-70 and the stimulating current 225 flowing between a driver 100-i and a respective electrode 245-i. If the voltage on C1 and C2 falls too close to the compliance voltage, the respective driver 100-i will not be able to maintain the required amplitude of the stimulation current 255.

In order to prevent this from happening, a compliance monitor circuit 110 is provided. Circuit 110 monitors occurrence of the above situation and notifies the external unit 20 through the back telemetry 160-180 to lower the stimulation current amplitude 255 by way of external controller 700 and the transceiver 710 and forward data link 40, or increase the capacitor voltage accordingly by way of the external controller 700 and coil driver 720.

The implanted device 10 is continuously powered and controlled by the external unit 20 through the inductive power link 30 and the data link 40, respectively. The external unit 20 comprises an external controller 700, a coil driver 720 and a data transceiver 710. The external controller 700 can include an information collector such as a camera in the case of retinal prosthesis, a microphone in the case of cochlear prosthesis, or some other form of sensory devices such as pressure, position or touch sensors for various other neuronal-stimulation applications. The external controller 700 can include a Digital Signal Processing Unit or a similar operation processor to synthesize the sensed information from the sensors and the feedback information from the implant 10 and generate controls accordingly to command the implanted device to deliver appropriate stimulation (amplitude and timing) to the tissue through the data transceiver 710. The data transceiver 710 ensures that the commands from the external controller 700 are delivered to the implant 10 reliably and the feedback from the implant 10 is received correctly. The data transceiver 710 communicates with the implant 10 in predefined communication protocols through its data antenna 730. In the meantime, the coil driver 720 ensures that adequate but not excessive power is delivered to the implant 10 for the intended stimulation intensity.

Also excessively high capacitor voltage is monitored, to avoid use of unnecessary high power to deliver the same charge. In particular, shunt regulators 80 and 90 include a circuital arrangement to program the level of the nominal capacitor voltage to a required value, for further power saving, as later discussed with reference to FIG. 4.

A power monitor circuit 120 is further provided, to monitor the charging and draining conditions of the capacitors, so that the external unit 20 can optimize the RF powering condition (see coil driver/monitor 720) and also stop stimulation when the implant 10 cannot be adequately powered. The power monitor circuit 120 will be explained in greater detail in FIG. 7.

The implant 10 further comprises an implant controller 130 and an implant transceiver 140. Implant controller 130 comprises a main controller 150 and a back telemetry (BT) controller 160. Implant transceiver 140 comprises a data receiver 170 and a back telemetry (BT) transmitter 180.

Implant controller 130 and implant transceiver 140 allow the stimulation control and power control to operate on a system level. In other words, they allow the external unit 20 to appropriately and accurately control the implant powering and stimulation.

The data receiver 170 receives forward telemetry (FT) data from the external unit 20 through data link 40. FT data is decoded by the main controller 150 to control the output of the electrode drivers 100, the rail voltages (as later shown in FIG. 4) and other operations, such as monitoring of the electrodes and the device status for safety reasons or for conducting system tests, and so on.

BT controller 160 collects and encodes implant information from the compliance monitor 110 and the power monitor 120, such as implant powering, stimulation, electrode condition and other safety information of the implant, e.g. device failure, electrode failure, excessive power condition etc. BT controller 160 sends the implant information back to the external unit 20 through BT transmitter 180, so that the system can act on such information.

For example, the output of the power monitor 120 is fed to the BT controller 160, which will include this information in the back telemetry stream. If the external unit 20, upon receiving the back telemetry data, determines that the currents flowing through the shunt regulators 80, 90 are too high, it will adjust the input to the coil driver 720 to lower the level of power driving the coil by an amount that is predetermined by the power control protocol. After the coil power is lowered, the shunt regulator currents will decrease, thus forming a closed control loop.

A possible type of electrode driver 100-i to be used in the present disclosure is a constant current type electrode driver. Current type electrode drivers output current pulses whose timing, duration and amplitude can be controlled through input commands. See, for example, "A Neuro-Stimulus Chip With Telemetry Unit For Retinal Prosthetic Device" by Liu, W., Vichienchom, K., Clements, M., DeMarco, S. C., Hughes, C., McGucken, E., Humayun, M. S., De Juan, E., Weiland, J. D., Greenberg, R., Solid-State Circuits, IEEE Journal of, Volume 35, Issue 10, October 2000, pages 1487-1497.

In this respect, FIG. 2 shows a more detailed circuital diagram of one of the electrode drivers 100-i of FIG. 1, the electrode driver being a constant current electrode driver.

Electrode driver 100-i comprises a driver controller 190. The driver controller 190 takes commands from the 'Stim-Controls' signals 195 coming from the main controller 150 and translates those signals into anodic and cathodic stimulation switching signals 200 and 210 that control pulse duration and timing. Driver controller 190 also provides an output current 220 that defines the current amplitude of the stimulation phases. MOSFET transistors M16 and M18 convert current 220 into anodic current 230. MOSFET transistors M18, M15, M11 and M12 convert current 220 into cathodic current 240. MOSFET transistors M13, M14 and M17 act as output switches.

As already explained with reference to previously discussed FIG. 1-1 through 1-3, electrode driver 100-i receives power from storage capacitors C1 and C2 (see voltage signals V+, V− shown in FIG. 2). Storage capacitor C1 provides power for anodic pulses. Storage capacitor C2 provides power for cathodic pulses.

Similarly to FIG. 1-2, FIG. 2 shows a return electrode 250. The return or common electrode 250 is connected to the junction Vce between C1 and C2. The cathodic stimulation currents 240, taken from C1, flow from the return electrode 250, through the tissue 70, to the V− rail of C1. The anodic stimulation currents 230, taken from C2, flow from the V+ rail of C2, through the tissue 70, to the return electrode 250. The electrical properties of the electrode-tissue interface can be modeled to a certain degree of accuracy by the simplified RC network shown in the shaded tissue circle.

Figure 3:
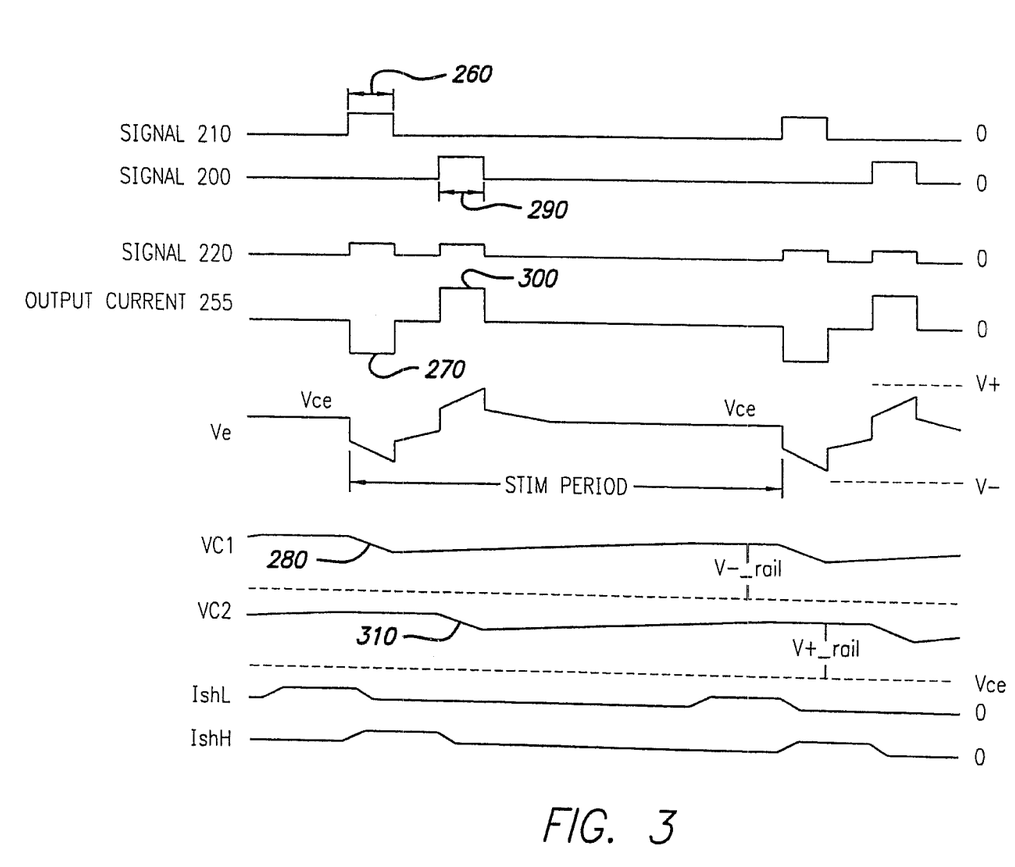
FIG. 3 is a timing diagram showing current and voltage signals related to the present disclosure.

FIG. 3 is a timing diagram showing the relationship between the stimulation timing, stimulation currents, surplus currents and voltages on capacitors C1 and C2.

During the cathodic stimulation phase 260, the cathodic stimulation switching signal 210 (first graph on FIG. 3 from the top) is ON, thus turning ON both MOSFETs M13 and M14 (see also FIG. 2). On the other hand, the anodic stimulation switching signal 220 (second graph on FIG. 3 from the top) is OFF during that time interval, thus keeping the MOSFET M17 and the anodic current 230 OFF. Meanwhile, output current signal 255 (third graph on FIG. 3 from the top) carries the programmed cathodic amplitude control current 270 (FIG. 3), so that a current 240 (FIG. 2) proportional to signal 220 (FIGS. 2 and 3) will flow from the return electrode 250 to V− through MOSFETs M14, M12 and the tissue 70 (FIG. 2), causing a stimulation. When cathodic current 240 flows, charge is drawn from C1, causing a dip $\Delta V$ 280 on the capacitor voltage VC1, as also shown in the VC1 graph of FIG. 3.

The charge Q delivered during a stimulation phase is $Q$=Cathodic Current 240×Duration Switching Signal 210 ON To the capacitor C1, a loss in charge Q means a drop in voltage $\Delta V$ $\Delta V = Q/C1$ =(Cathodic Current 240×Duration Switching Signal 210 ON)/C1

If the capacitor C1 is being constantly charged with a current Icharge, the voltage on C1 at the end of the stimulation will be $\Delta V$=(Cathodic current 240−Icharge)×Duration Switching Signal 210 ON/C1

During the anodic stimulation phase 290, the anodic stimulation switching signal 200 (second graph on FIG. 3 from the top) is ON, thus turning ON MOSFET M17, while stimulation switching signal 210 keeps the cathodic circuit OFF during that time interval. Output current signal 255 carries the programmed anodic amplitude control current 300 (FIG. 3), so that a current 230 (FIG. 2) proportional to signal 255 (FIGS. 2 and 3) for the anodic phase will flow from V+ to the return electrode 250 through MOSFETs M16 and M17 and the tissue 70 (FIG. 2), releasing the charge collected on the stimulating electrode 245 during the cathodic phase 260 and achieving electrical chemistry balance. When anodic current 230 flows, charge is drawn from C2, causing a dip $\Delta V$ 310 on the capacitor voltage VC2, as also shown in the VC2 graph of FIG. 3. Similarly to what discussed above, the voltage drop $\Delta V$ on capacitor C2 is $\Delta V = Q/C2$=(Anodic Current 230×Duration Switching Signal 200 ON)/C2

It should be noted that when power is supplied to the drivers 100, the charges on capacitors C1 and C2 are drawn only during the stimulation pulses (see time intervals 260 and 290 of FIG. 3), but are being injected by the power charging circuit 60 all the time. Therefore, the charging current can be controlled to inject sufficient charges to the capacitors as needed by the stimulation, to minimize the value of surplus currents IshL and IshH to achieve good power efficiency. The charging current is controlled through control of the power driving the external coil and the shunt regulator current value included in the back telemetry data as the output of the control closes the power control loop.

As also shown in FIGS. 1-2 and 2, the capacitor voltages V+, V− are the supply rails to the electrode drivers 100-i. According to a further embodiment of the present disclosure, the capacitor voltages can be limited. Limitation of those voltages can be applied for two reasons. A first reason is that the electronic chip on which the implant 10 is operated should operate under a specific voltage limit for safety reasons. A second reason is that the power needed to inject a certain amount of charge in the capacitor is proportional to the capacitor voltage itself. Therefore, limiting the capacitor voltage to a level just satisfying the need of electrode compliance voltages will also allow power to be saved.

As also explained with reference to FIGS. 1-1, 1-2 and 1-3, the voltages of C1 and C2 are limited by shunt regulator circuits 80 and 90, respectively. In particular, shunt regulator circuits 80 and 90 can limit the capacitor voltages to a preprogrammed value during charging. After the voltage on capacitors C1 and C2 reaches the safety voltage limit, circuits 80 and 90 will bypass (shunt) the surplus charging current and the capacitor voltages will not rise further. The shunting circuits 80 and 90 may also comprise a current tap out, which provides a quantitative indication of the surplus current. Such indication can be used to estimate the power condition of the implant 10. Shunting circuits 80 and 90 can also comprise a rail control mechanism, which allows the external unit 20 to set the capacitor voltage limit through binary control bits.

Figure 4:
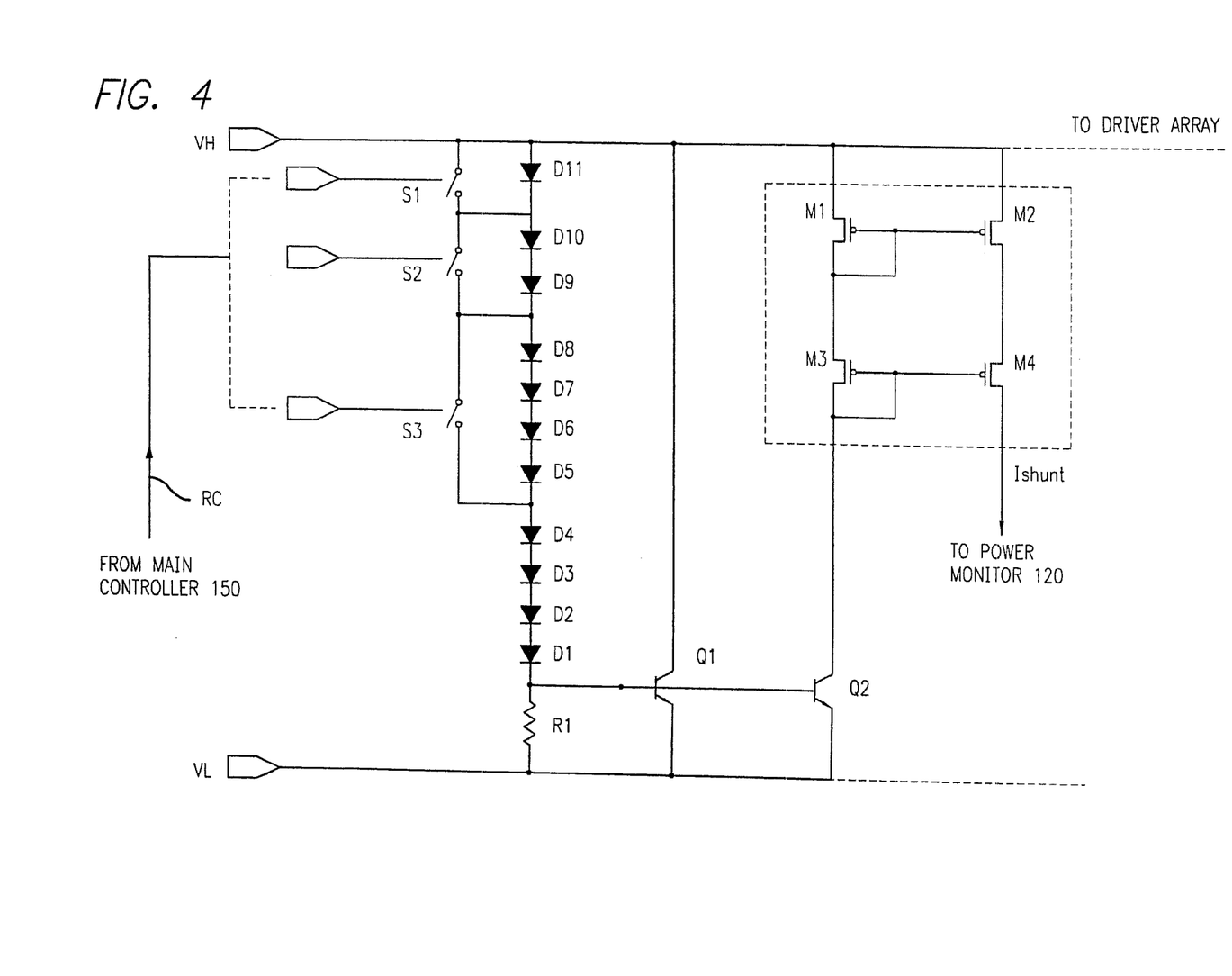
FIG. 4 shows a circuital scheme of one of the shunt regulator circuits of FIG. 1.

FIG. 4 shows in greater detail the internal structure shunt regulator circuits 80, 90, in accordance with a further embodiment of the present disclosure. The shunting circuit comprises a current sensor and a current sink. In the embodiment of FIG. 4, the current sensor is comprised of a diode stack D1-D11 in series with a sampling resistor R1, and the current sinking circuit is comprised of an npn transistor amplifier Q1. During operation, the first terminal VH of the current sensor is connected with either V+ or VM (see FIGS. 1-1, 1-2 and 1-3), while the second terminal VL of the current sensor is connected with VL either VM or V− (see FIGS. 1-1, 1-2 and 1-3). Therefore, during operation, the two terminals of the current sensor are connected in parallel with the capacitors C1, C2. When the voltage across each capacitor reaches a value that is greater than the sum of the "knee" voltages of PN junction diodes D1-D11, the current through the diodes increases rapidly, so as the voltage across sampling resistor R1 and the base current of transistor Q1. The common emitter transistor Q1 will then sink a larger current through its collector that is determined by the current gain of the transistor. The sensitivity of the current sensor is controlled by resistor R1. The person skilled in the art will understand that transistor Q1 can be replaced by any other arrangement suitable for the same purpose. For example, if CMOS technology is used, the current gain of a single transistor may be limited, and Q1 could be replaced with a Darlington pair and/or a transistor array to increase the current gain for a better shunt effect. The person skilled in the art will also understand that the number of diodes D1-D11 can be any number, depending on the highest rail voltage specified.

The shunting circuit of FIG. 4 also comprises a transistor Q2 and a current mirror MOSFET circuit M1-M4. In particular, Q2 and M1-M4 provide a current tap out Ishunt for quantitative measurement of the surplus current flowing through the shunting circuit of FIG. 4. The output signal Ishunt is sent to power monitor 120, as already shown in FIGS. 1-1, 1-2 and 1-3 and also later shown in FIG. 7.

The embodiment of FIG. 4 also provides for the presence of a rail control mechanism along connection RC between main controller 150 and shunting circuits 80, 90 (see FIGS. 1-1, 1-2 and 1-3). In particular, control of a rail voltage can be obtained by selectively shorting a certain number of diodes of the diode chain in the shunting circuit using MOSFET switches (see switches S1-S3 in FIG. 4). As shown in FIG. 4, the connection of the switches S1-S3 with the diodes D1-D11 provides a direct binary encoding, allowing the rail voltage limit to be conveniently programmed without the need of an encoding interface. It should be noted that the resolution of the rail voltage control is one diode voltage drop which is logarithmically proportional to the diode current. In the embodiment shown in FIG. 4, only a small portion of the surplus current will flow through the diode chain D1-D11. Therefore, the diode voltage drop is close to the turn-on voltage for the operating diodes, and the error caused by the ON resistance of the switches for shorted diodes is insignificant.

When the electrode voltage reaches the compliance limit due to increased electrode impedance, the output current 255 of the electrode driver cell (see, e.g., FIG. 2) will deliver less amount of current than what is set to be. This situation will affect the output accuracy of the implant 10 and is also likely to result in unbalanced current pulses that are not favorable to the electrodes 245 or the tissue 70. The electrode voltages, however, are determined by the in vivo electrode-tissue impedances which can vary greatly over time or among different electrodes, thus making any preset limit inefficient.

Figure 5:
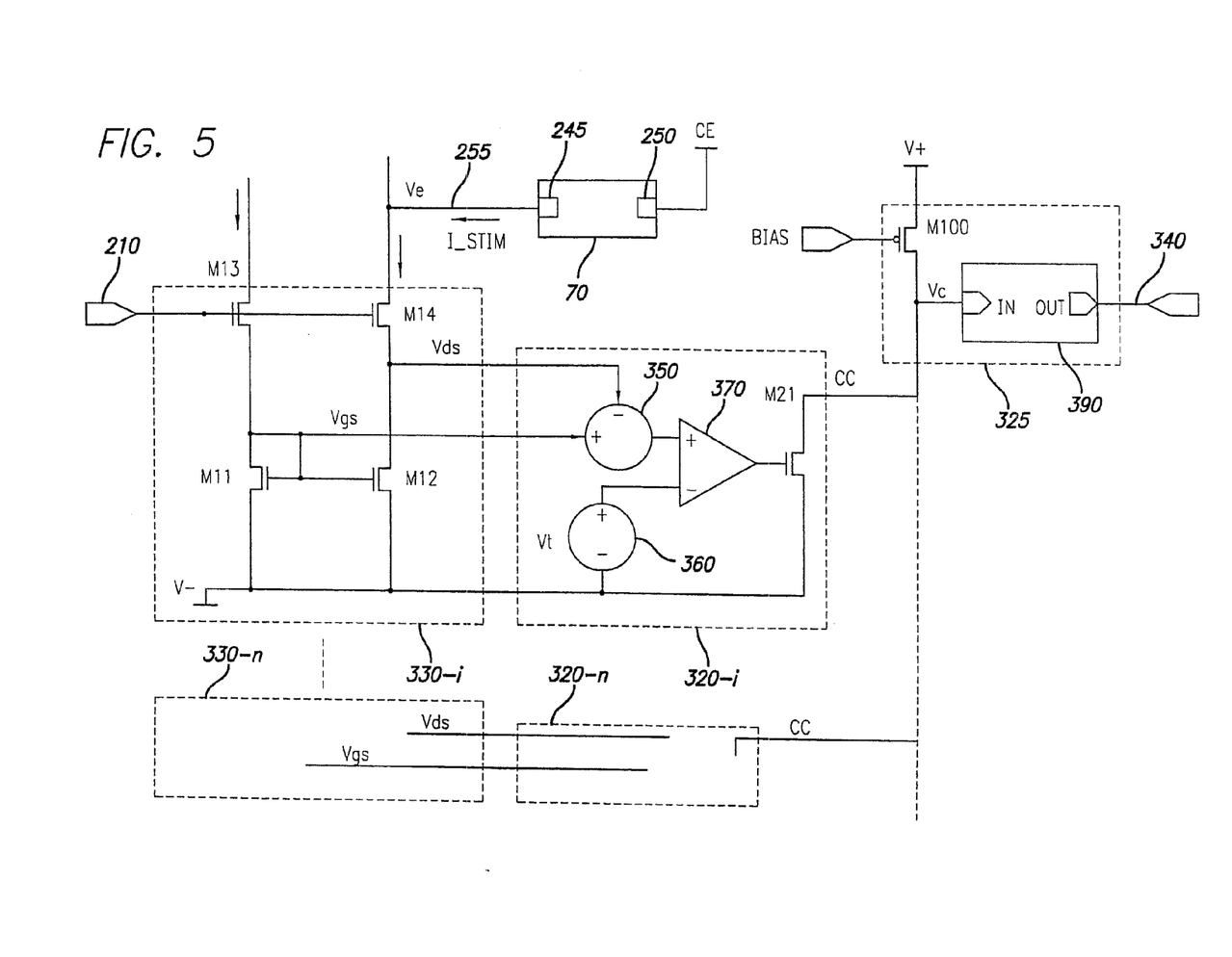
FIG. 5 shows a circuital scheme of the compliance monitor circuit of FIG. 1.

A further embodiment of the present disclosure addresses the above issue by providing a compliance monitoring circuit as already mentioned with reference to circuit 110 of FIG. 1-3, which circuit is shown in FIG. 5 in greater detail. Although the compliance monitoring circuit 110 of FIG. 1-3 has been shown separately from the driver array 100, such circuit, portions of which are represented in FIG. 5 with reference numerals 320-i and 325, can be embedded into each current driver cell 100-i. Therefore, according to a further embodiment of the present disclosure, there will be one compliance monitoring circuit per driver. Generally speaking, the compliance monitor 320-i/325 monitors the voltage of electrode 245 to see if such voltage has reached the compliance limit. When such limit is reached, the compliance monitor generates a signal CompAlert 340 (FIGS. 1-3 and 5) to alert the BT controller 160 and/or the external unit 20, so that a decision as to whether the rail voltage should be increased or the stimulation current decreased can be made.

Box 330-i of FIG. 5 represents a portion of driver cell 100-i of FIG. 2. Such portion 330-i comprises cathodic or sink current MOSFETs M11, M12, M13 and M14.

Generally speaking, ignoring the short channel effect of the MOSFET, the drain output current of the electrode driver is set by a gate-source voltage Vgs but not a drain-source voltage Vds as long as the output MOSFET is in the saturation region, i.e., when the drain-source voltage Vds is larger than the gate-source voltage Vgs subtracting the threshold voltage Vt of the device. The drain current falls off rapidly as the drain-source voltage decreases further. This condition to hold the drain output current constant can be written as:

$$Vds >= Vgs - Vt \quad (1)$$

In the electrode driver circuit, the above condition of drain-source voltage Vds of the output MOSFETs, together with the power supply rail voltage Vp, defines the output compliance limit of the electrode stimulator. For example, if the power supply voltage is 10 volts, the threshold voltage Vt is 1 volt, and the gate-source voltage Vgs is set at 1.5 volts, then the compliance limit can be defined as Vcomp=Vp−(Vgs−Vt) =9.5 volts. The compliance monitor circuit according to the present disclosure detects the condition of failing to meet (1), i.e., it detects the condition that fulfils:

$$Vds < Vgs - Vt \quad (2), or$$

$$Vgs - Vds > Vt \quad (3)$$

The circuit shown in FIG. 5 is a direct realization of the condition of equation (3). In a cathodic phase first stimulation protocol, the voltage on the electrode 245 tends to shift towards a negative value relative to the return electrode 250 because of the capacitive component in the electrode impedance. Therefore, the sink part (MOSFETS M11-M14) of the current driver is more susceptible to reaching the compliance limit.

In the circuit of FIG. 5, MOSFET M12 is the output transistor that is responsible for maintaining a stable current output. Vgs represents the gate-source voltage difference of M12, while Vds represents the drain-source voltage difference of M12. The compliance monitor circuit 320 monitors the difference Vgs−Vds of M12 by way of a subtracting circuit 350 whose output is compared with the threshold voltage Vt reference 360 through comparator 370. The output of comparator 370 drives an open drain nMOS transistor M21 whose output CC is fed to node Vc, where the outputs of the compliance monitors of all drivers 100-1, 100-2 . . . , 100-i, . . . 100-n are line OR-ed through MOSFET M100.

In normal operation, equation (3) is not fulfilled, and the output of comparator 370 is LOW, shutting off M21 so that its output CC does not affect node 380. However, if the output voltage of the electrode 245 reaches the compliance limit, equation (3) is satisfied and the output of comparator 370 becomes HIGH, turning on M21, so that its output CC pulls down the voltage on node 380 to LOW. The voltage change on node 380 will be sensed by a compliance logic circuit 390 to generate the CompAlert signal 340 discussed above.

Figure 6:
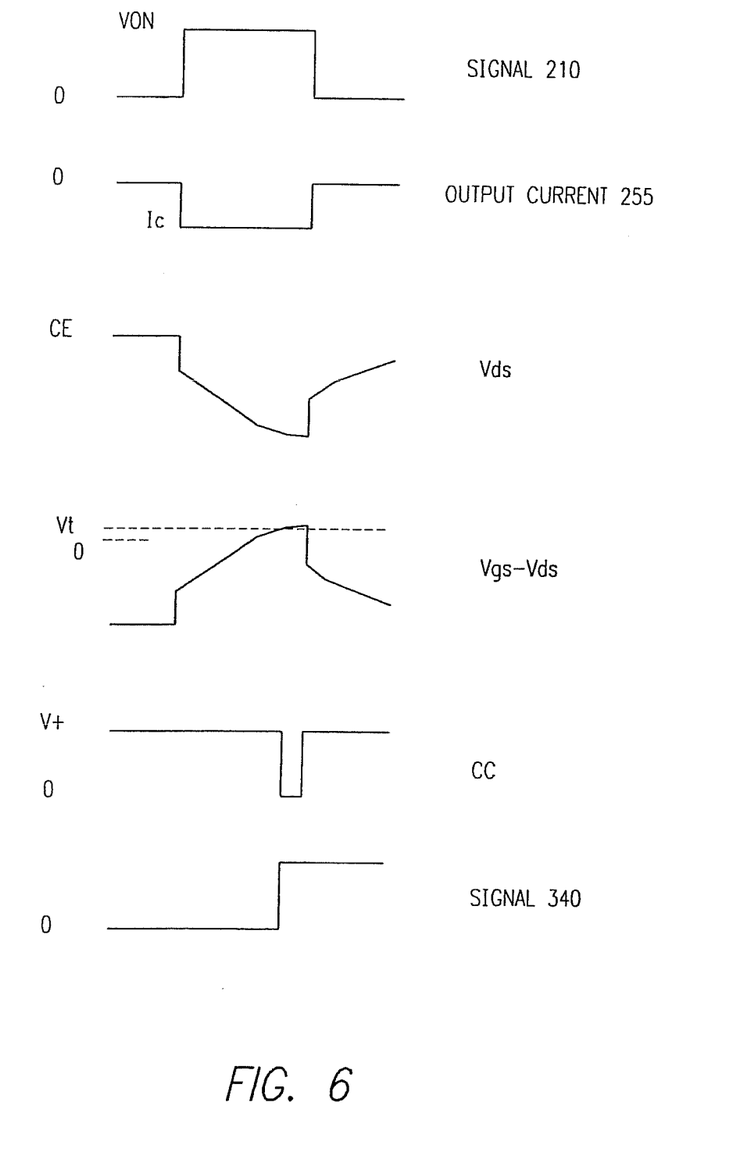
FIG. 6 is a timing diagram showing signals related to the circuit of FIG. 5.

FIG. 6 is a timing diagram for signal 210, output current 255, Vds, Vgs-Vds, CC and CompAlert, showing the behavior of those signals during operation of the compliance monitoring circuit discussed with reference to FIG. 5.

According to a further embodiment, the present disclosure also provides for power monitoring circuits 120 to monitor the charging and draining conditions of the capacitors, as already explained with reference to FIGS. 1-1, 1-2 and 1-3. In particular, the power monitoring circuits monitor the surplus currents flowing through the shunting circuits 80, 90 and the voltages on the capacitors C1, C2. Monitoring the surplus current allows a flexible, quantitative control of the inductive power loop, i.e. the loop including the coil driver, the coil pair, and the power storage capacitors.

For example, the power level can be predefined (by way of a feedforward method) or adaptive to the load requirement (by way of feedback information). In addition, monitoring of the storage capacitor voltages prevents the implant device 10 from operating with an insufficient power condition that may compromise safety.

Figure 7:
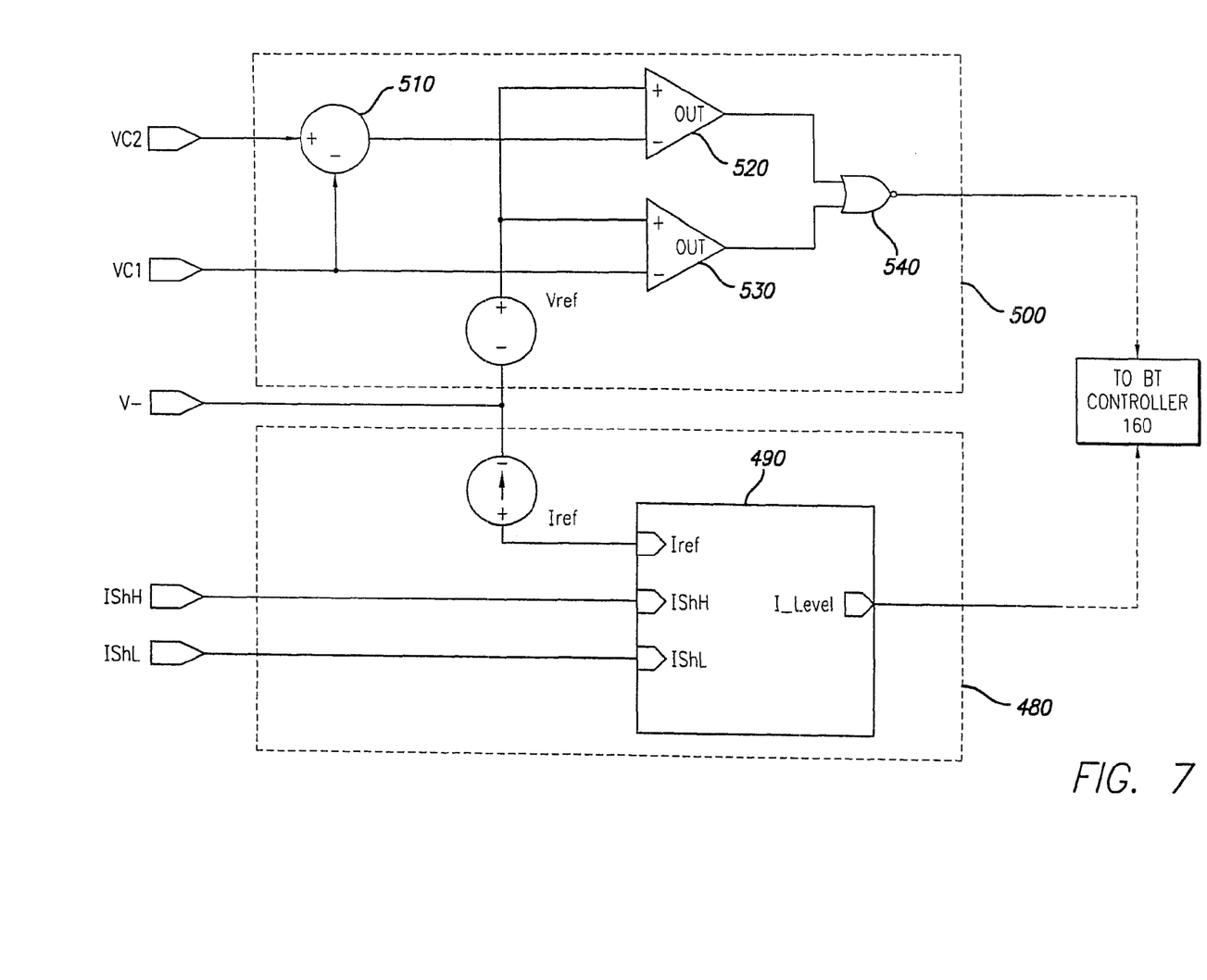
FIG. 7 shows a circuital scheme for the power monitor circuit of FIG. 1.

With reference to FIG. 4, applicants have already discussed how the surplus current is tapped out as Ishunt through Q1 and M1-M4 in the shunting circuits 80, 90. FIG. 7 shows a current monitor 480 comprising an analog-to-digital converter (ADC) 490 that digitizes the analog Ishunt inputs IShH and IshL received from shunting circuits 80 and 90 (see also FIG. 1-2). The converted digital output I_Level is sent to BT controller 160 and eventually reported to the external unit 20.

Figure 81:
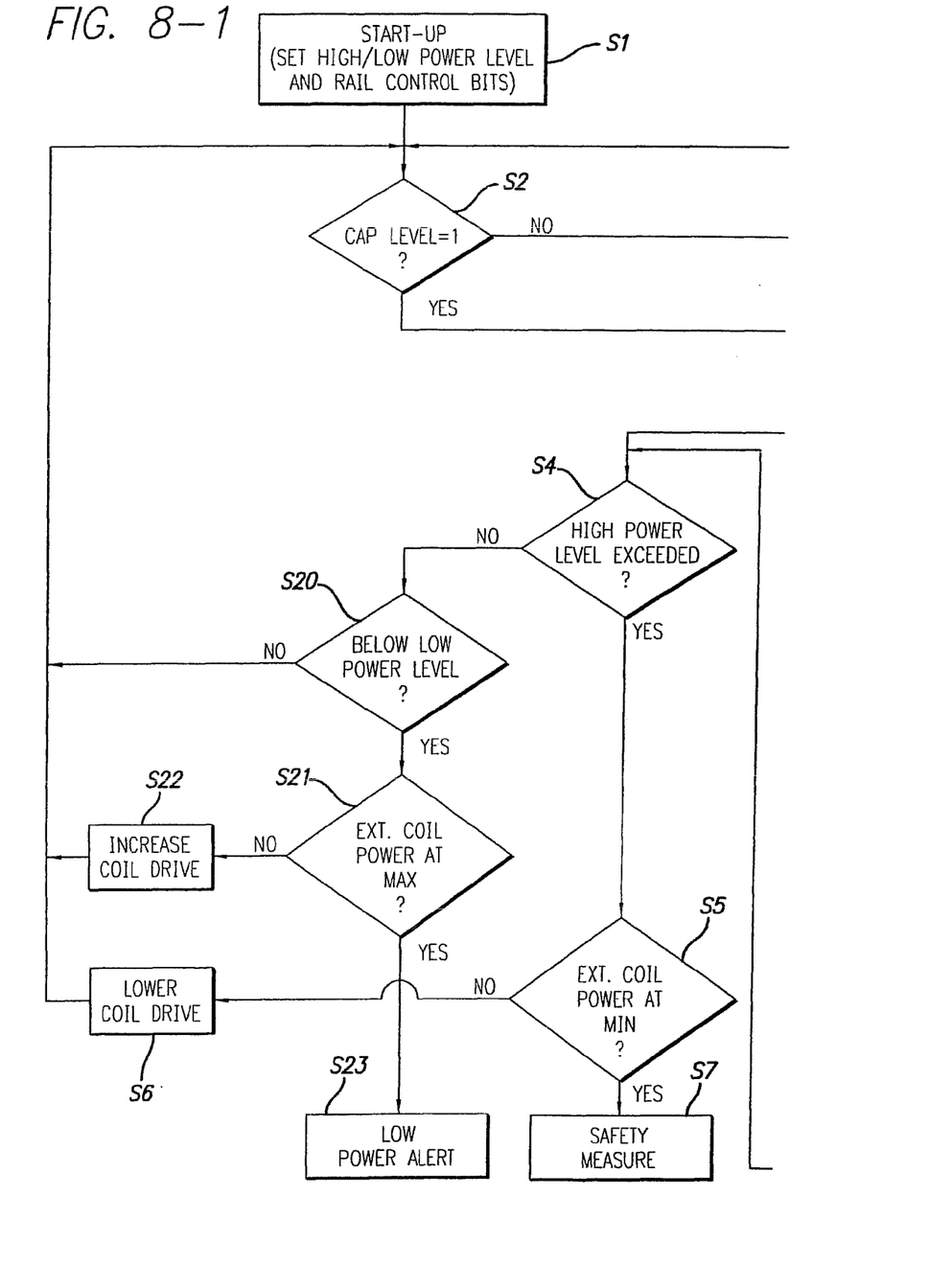
Figure 82:
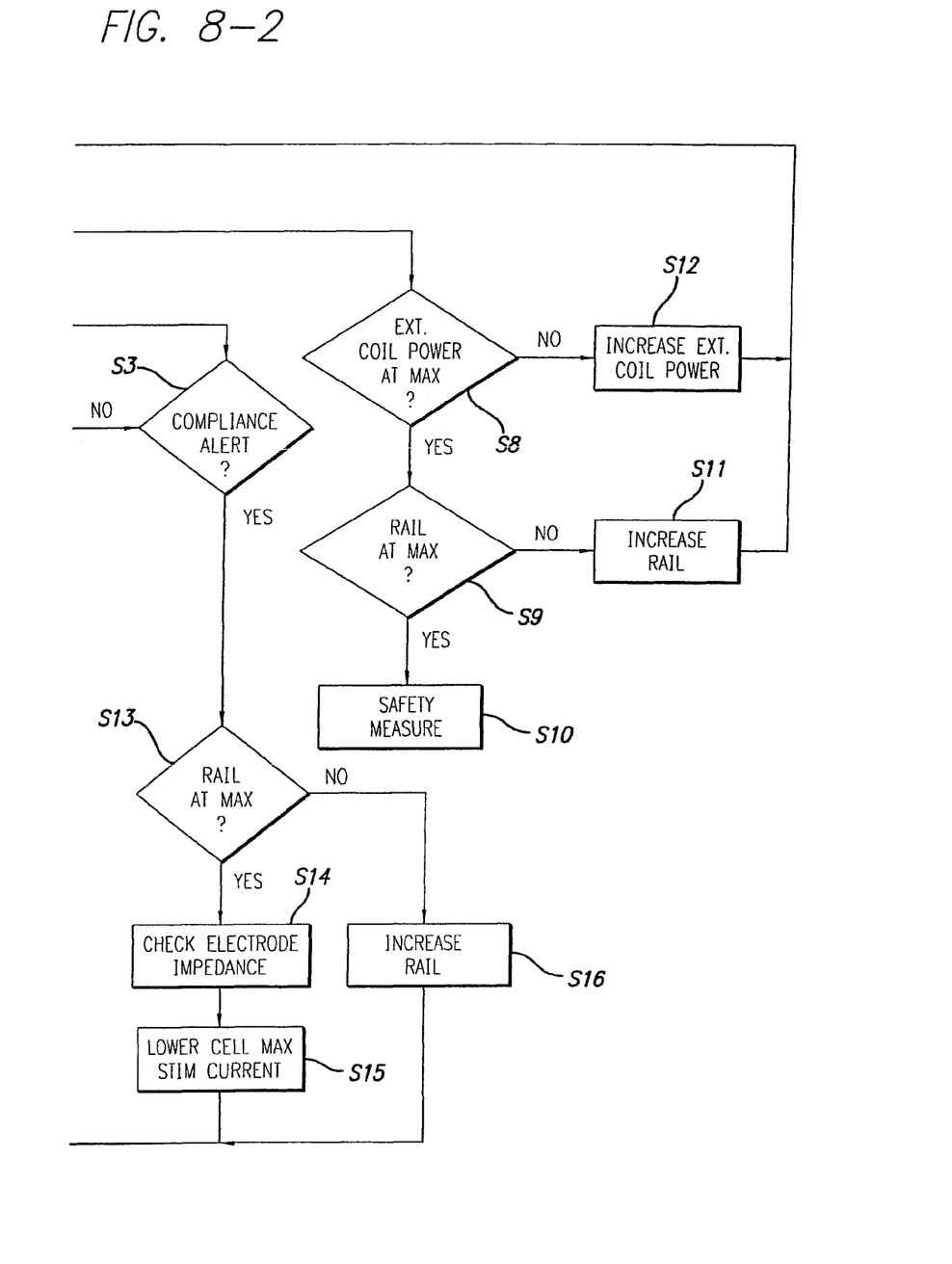

Reference can also be made to the flow chart shown in the following FIGS. 8-1 and 8-2, where this current data is checked against a preset power level (threshold) (see steps S4 and S20 of FIG. 8-1) and a decision is made as to whether increase or decrease the power output of the RF coil driver (see the left portion of FIG. 8-1).

Meanwhile, the voltages on C1 and C2 are also monitored by a capacitor monitoring circuit 500 comprising a subtracting circuit 510, comparators 520, 530 and NOR logic 540. In normal power conditions, the output CapLevel of the capacitor monitoring circuit is HIGH. If either one of the capacitor voltages VC1, VC2 falls below a preset threshold Vref (depending on the implementation of the circuit), the output CapLevel becomes LOW. The LOW value of CapLevel indicates that implant power has fallen below a critical low level required for safe operation. Upon receipt of a CapLevel LOW signal, the external control will have to stop the stimulating operation of the implant and raise the RF power output level until CapLevel reaches again and stays at a HIGH value.

FIGS. 8-1 and 8-2 are a flow chart showing the system power control flow. During start-up step S1 the PowerLevel limit (high and low threshold values of the digital output of ADC 490 in FIG. 7 to be checked against) and the rail control bits (see FIG. 4) are set. Step S2 checks the value of the CapLevel signal discussed in FIG. 7. If the value is HIGH, the implant is under normal operating conditions and the flow proceeds to step S3 where the value of the CompAlert signal 340 of FIG. 5 is checked, to see whether the voltage on electrode 245 has reached the compliance limit. In case such limit has not been reached the flow proceeds to step S4 to check whether the power (represented by the surplus current from ADC 490) has exceeded the high threshold of PowerLevel limit set in step S1. Should this not be the case, the flow proceeds to step S20 to check whether the power has fallen below the low threshold of the PowerLevel limit. If not (meaning that the implant power is within the expected range), the flow goes back to step S2 for continuous monitoring. However, if the answer to the determination made in step S20 is affirmative, the flow first checks if the power driving the external coil (RF Power) has reached its maximum level (an external unit specification) in a step S21. If it has not reached the maximum level, the coil drive is increased by an amount predefined in the control protocol in a step S22 and the flow goes back to step S2 to continue a next round of monitoring of the implant power. If, on the other hand, the power driving the external coil has reached the maximum level so that no further increase of driving power is allowed, a low power alert of the implant is asserted in step S23.

On the other hand, if the answer to the question of step S4 is positive, which means that the implant power is excessive, the flow moves to step S5 where it is checked if the power driving the external coil is at its minimum level. If the power is not at its minimum, such power is lowered in step S6 (lower coil drive) and the flow goes back to step S2. On the contrary, if the RF driving power level is already at its minimum, indicating that the PowerLevel overshoot of step S4 could be due to malfunctioning of the external unit, safety measures are activated in step S7. Turning back to step S2, if the value of the CapLevel signal of FIG. 7 is LOW, it indicates a critical low power level that could be due to poor coupling of the coils, insufficient rail voltages, excessive stimulation current, or malfunction in the powering loop that includes the external coil driver, the coils and the implant circuits. When this happens, the flow first proceeds to step S8 where it is checked if the power driving the external coil has been at its maximum. If that condition is satisfied, the flow proceeds to step S9 where the rail voltage is checked. If also that condition is satisfied (i.e. rail voltage at its maximum value), safety measures are activated in step S10 to stop the stimulation operation. If, on the other hand, the rail voltage is not at its maximum value, such voltage is increased at step S11 and the flow goes back to step S2. Similarly, if the coil driving power checked in step S8 is not at its maximum, such power is increased in step S12 and the flow goes back to step S2. Turning to step S3, in case the compliance limit has been reached, the flow moves to step S13 where it is checked if the rail control has set the rail voltage to its maximum value. If yes, the electrode impedance is checked at step S14 and the maximum stimulation current is recalculated accordingly at step S15. Once this has been done, the flow moves to step S4, already discussed above, to check the power level. Turning to step S13, if the rail voltage is not at its maximum value, such value is increased at step S16 and the flow moves to step S4 already discussed above.

While several illustrative embodiments of the invention have been shown and described in the above description, numerous variations and alternative embodiments will occur to those skilled in the art. Such variations and alternative embodiments are contemplated, and can be made without departing from the scope of the invention as defined in the appended claims.

What is claimed is:

1. A constant current type electrode driver for an implant for a human or animal body, the electrode driver comprising:
   a driver controller adapted to be implanted within a body to generate anodic and cathodic stimulation switching signals and generate an output current defining a current amplitude for stimulation;
   a capacitive storage arrangement providing power to the driver controller;
   a voltage limiting shunting arrangement connected with the capacitive storage arrangement, to limit voltage on the capacitive storage arrangement;
   a capacitive storage arrangement monitoring circuit adapted to be implanted within the body comprising a subtracting circuit, comparators and NOR logic, wherein the capacitive storage arrangement monitoring circuit is connected with the capacitive storage arrangement, the shunting arrangement, and the driver controller, and wherein the capacitive storage arrangement monitoring circuit is configured to:
      monitor charging and draining conditions of the capacitive storage arrangement;
      monitor the capacitive storage arrangement and voltage limiting shunting arrangement including shunt current data;
      output, in normal power conditions, a high output level signal or a low output level signal in case a voltage of the capacitive storage arrangement falls below a preset threshold, wherein the low output level signal indicates that implant power has fallen below a critical low level required for safe operation;
   a back telemetry controller connected to the capacitive storage arrangement monitoring circuit that is also adapted to be implanted within the body;

a transmitter adapted to be implanted within the body that is configured to transmit driver status data and shunt current data; and a power supply adapted to be external to the body that is configured to:
  receive said driver status data, shunt current data, said high output level signal and said low output level signal;
  alter power transmitted according to said driver status data and said shunt current data; and;
  upon receipt of said low output level signal, stop a stimulating operation and raise a power output level until the output level signal corresponds to the high output level signal.

2. The electrode driver of claim 1, wherein the implant comprises storage capacitors, the driver controller receiving power from the storage capacitors as input.

3. The electrode driver of claim 2, wherein a first capacitor of the storage capacitors provides power for the anodic current and a second capacitor of the storage capacitors provides power for the cathodic current.

4. A driver array comprising a plurality of electrode drivers according to claim 1.

5. The electrode driver of claim 1, further comprising:
a charging circuit,
  wherein the capacitive storage arrangement is directly connected with both the charging circuit and the voltage limiting shunting arrangement and the capacitive storage arrangement is charged by the charging circuit.

* * * * *